(12) United States Patent
Matyas et al.

(10) Patent No.: US 12,193,940 B2
(45) Date of Patent: Jan. 14, 2025

(54) CUSTOMIZED IMPLANT AND METHOD

(71) Applicant: DePuy Ireland Unlimited Company, Ringaskiddy (IE)

(72) Inventors: Aaron J. Matyas, Ft. Wayne, IN (US); Filip Leszko, West Chester, OH (US); Fernando M. Zapari, Jr., Ft. Wayne, IN (US); Joseph G. Wyss, Ft. Wayne, IN (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 896 days.

(21) Appl. No.: 17/173,267

(22) Filed: Feb. 11, 2021

(65) Prior Publication Data

US 2022/0249236 A1 Aug. 11, 2022

(51) Int. Cl.
| | |
|---|---|
| *A61F 2/30* | (2006.01) |
| *G16H 20/40* | (2018.01) |
| *A61B 17/16* | (2006.01) |
| *A61B 34/20* | (2016.01) |
| *A61F 2/32* | (2006.01) |

(52) U.S. Cl.
CPC ...... *A61F 2/30942* (2013.01); *A61F 2/30771* (2013.01); *G16H 20/40* (2018.01); *A61B 17/16* (2013.01); *A61B 34/20* (2016.02); *A61F 2002/30943* (2013.01); *A61F 2/32* (2013.01)

(58) Field of Classification Search
CPC ....... A61F 2/02; A61F 2/3094; A61F 2/30942
See application file for complete search history.

(56) References Cited

U.S. PATENT DOCUMENTS

| | | | | |
|---|---|---|---|---|
| 4,936,862 | A * | 6/1990 | Walker | G05B 19/4207 700/98 |
| 8,086,336 | B2 * | 12/2011 | Christensen | A61F 2/2875 700/118 |
| 2016/0338778 | A1 * | 11/2016 | Zuhars | A61B 90/98 |
| 2017/0181755 | A1 * | 6/2017 | Librot | A61B 34/20 |
| 2019/0038419 | A1 * | 2/2019 | Feldman | A61F 2/30942 |
| 2020/0281742 | A1 * | 9/2020 | Wu | G16H 20/40 |

* cited by examiner

*Primary Examiner* — Erin McGrath
(74) *Attorney, Agent, or Firm* — BakerHostetler (57) ABSTRACT

A system configured to design a customized implant includes a cutting tool, a tracker, and design software. The cutting tool is configured to resect bone from an anatomical bone along a cutting path, thereby creating a contoured bone surface. The tracker is configured to track at least a portion of the cutting path and store the at least a portion of the cutting path in a memory. The design software is configured to design an implant having a contoured implant surface that matches the contoured bone surface based at least in part on the stored cutting path.

20 Claims, 12 Drawing Sheets

CUSTOMIZED IMPLANT AND METHOD

TECHNICAL FIELD

The present invention relates to a system and method used to design a customized patient-specific implants for repairing of fractures or deformities in bones.

BACKGROUND

During a procedure to restore the function of a bone joint, damaged bone and/or bone defects can be removed. A bone implant is used to replace the removed bone to maintain bone dimension and contours of the bone joint.

Conventional implants are designed using either generic models of the bone being restored or scans of the patient's bone. The model of the bone is updated after the surgical procedure based on an additional scan of the area of the bone where the bone material has been resected. An implant is designed based on the updated model to replace the resected bone material.

The foregoing background discussion is intended solely to aid the reader. It is not intended to limit the innovations described herein. Thus, the foregoing discussion should not be taken to indicate that any particular element of a prior system is unsuitable for use with the innovations described herein, nor is it intended to indicate that any element is essential in implementing the innovations described herein.

SUMMARY

According to an aspect of the present disclosure, a method of customizing a bone implant is provided. The method comprises the steps of: operating a cutting tool along a cutting path through an anatomical bone so as to resect bone from the anatomical bone, thereby defining a contoured bone surface of the anatomical bone; tracking at least a portion of the cutting path during the operating step, thereby defining a tracked cutting path; storing the at least a portion of the tracked cutting path in a memory; designing a virtual customized implant having a contoured bone-facing surface corresponding, at least in part, to the stored cutting path, wherein the contoured bone-facing surface substantially matches the contoured bone surface.

According to another aspect of the present disclosure, a system configured to customize a bone implant is provided. The system comprises a cutting tool, a tracker, and design software. The cutting tool is configured operate along a cutting path through anatomical bone so as to resect bone from the anatomical bone, thereby defining a contoured bone surface of the anatomical bone. The tracker is configured to track at least a portion of the cutting path thereby defining a tracked cutting path. The tracker is further configured to store the tracked cutting path in a memory. The design software is configured to design a virtualized customized implant having a contoured bone-facing surface corresponding, at least in part, to the stored cutting path. The contoured bone-facing surface substantially matches the contoured bone surface.

This summary is provided to introduce a selection of concepts in a simplified form that are further described below in the Detailed Description section. This Summary is not intended to identify key features or essential features of the claimed subject matter, nor is it intended to be used to limit the scope of the claimed subject matter. Furthermore, the claimed subject matter is not constrained to limitations that solve any or all disadvantages noted in any part of this disclosure.

BRIEF DESCRIPTION OF THE DRAWINGS

The foregoing summary, as well as the following detailed description of illustrative embodiments of the intervertebral implant of the present application, will be better understood when read in conjunction with the appended drawings. For the purposes of illustrating the expandable intervertebral implant of the present application, there is shown in the drawings illustrative embodiments. It should be understood, however, that the application is not limited to the precise arrangements and instrumentalities shown. In the drawings.

DETAILED DESCRIPTION

The disclosure relates to a system configured to manufacture a customized implant for replacing bone removed from a patient. In an aspect, a surgeon can direct an arm, which can be a robotic arm, that supports a tool to remove material from the bone. The surgeon's tool path is recorded in real time creating a tool path point cloud. An additive manufacturing tool can be attached to the robotic arm, and the robotic arm can replace the removed material to build, for example, a new articulating face or other necessary feature. The bone can be replaced with a polymer or other biocompatible material with minimal surgeon intervention. The method for manufacturing and inserting the customized implant into the patient can comprise the following steps: attach burr (e.g. cutting tool) to a registered robotic arm/construct; surgeon removes defect/diseased tissue with burr attached to arm and a tool path point cloud of the removed material at the burr tip is created and recorded in real time; point cloud data can be added to an articulating face or geometry to create a continuous part that is converted to a usable additive manufacturing file; additive manufacturing component with print media is attached to the robotic arm; and creating the implant from the point cloud by printing into the defect by the robotic arm.

The present disclosure can be understood more readily by reference to the following detailed description taken in connection with the accompanying Figs. and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

Certain terminology used in this description is for convenience only and is not limiting. The words "top", "bottom", "inner", "outer", "above", "below", "axial", "transverse", "circumferential," and "radial" designate directions in the drawings to which reference is made. The words "inner", "internal", and "interior" refer to directions towards the geometric center of the implant and/or implant adjustment tools, while the words "outer", "external", and "exterior" refer to directions away from the geometric center of the implant and/or implant adjustment tools. The words, "anterior", "posterior", "superior," "inferior," "medial," "lateral," and related words and/or phrases are used to designate various positions and orientations in the human body to which reference is made. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. The terminology includes the above-listed words, derivatives thereof and words of similar import.

As used herein, the terms "substantial", "substantially," and derivatives thereof, and words of similar import, when used to describe a size, shape, orientation, distance, spatial relationship, or other parameter includes the stated size, shape, orientation, distance, spatial relationship, or other parameter, and can also include a range up to 10% more and up to 10% less than the stated parameter, including 5% more and 5% less, including 3% more and 3% less, including 1% more and 1% less.

Figure 1A:
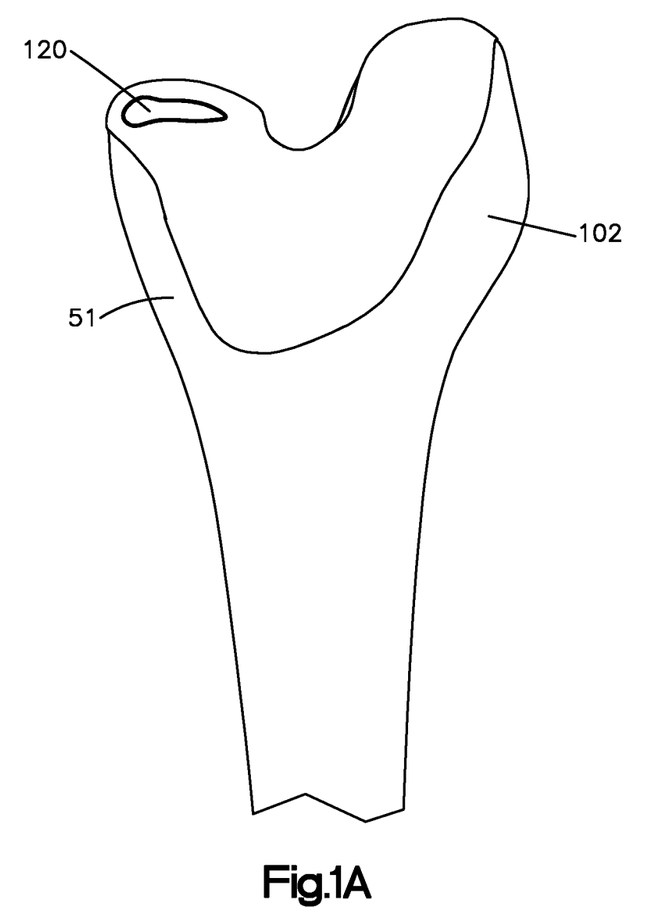
FIG. 1A is a perspective view of a surface of a condylar surface of a patient's femur that partially defines a knee joint, wherein the condylar surface has a bone defect.
Figure 1B:
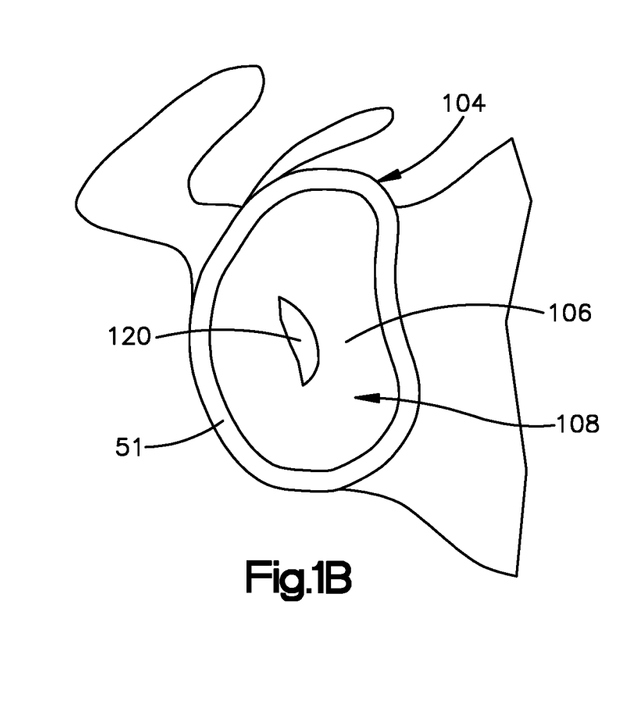
FIG. 1B is a perspective view of a glenoid surface that defines a glenoid cavity of a shoulder joint, wherein the glenoid surface has a bone defect.
Figure 1C:
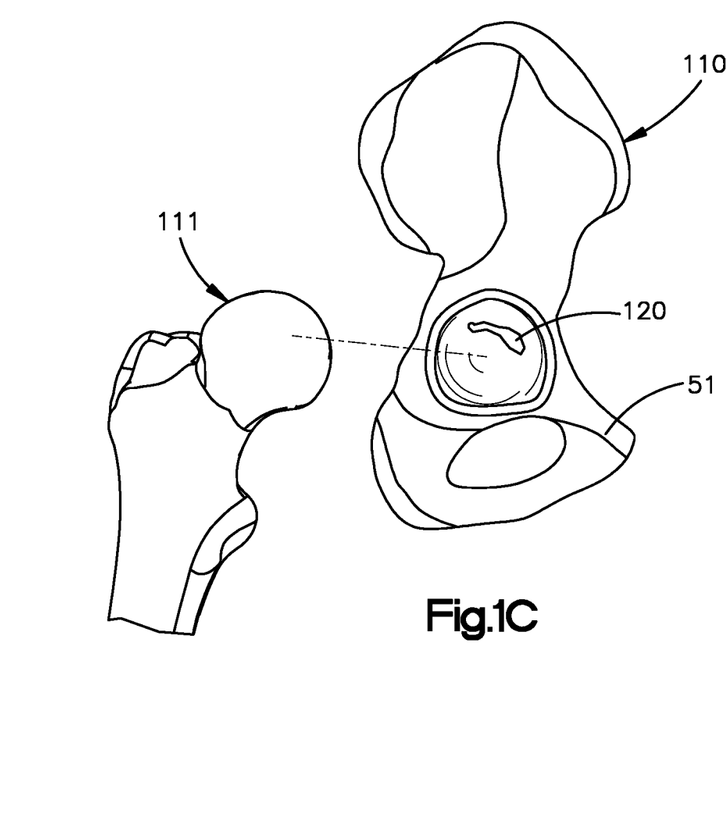
FIG. 1C is a perspective view of a glenoid surface that defines a glenoid cavity of a shoulder joint, wherein the glenoid surface has a bone defect

Referring to FIGS. 1A-1C, the present disclosure provides a method and apparatus for customizing an implant to promote the healing of a bone defect 120. The bone defect can be located at any bone 51 throughout the human anatomy. In some examples, at least a portion of the bone defect 120 can be disposed at an articular bone 51 that partially defines an anatomical joint. Other portions of the bone defect 120 can extend into the bone. Examples of the bone defect 120 can include one or more regions of bone degeneration such as osteoporotic bone, one or more bone fractures or other trauma, and the like.

For instance, referring to FIG. 1A, the anatomical bone 51 having the bone defect 120 can be defined by a femoral condyle 123 of a knee joint 102. For instance, the bone defect 120 can be defined by one or both of the medial femoral condyle and the lateral femoral condyle. In particular, the bone defect 120 can be at least partially disposed at an articular surface 121 of the femoral condyle 123. Alternatively, the bone defect 120 can be defined by a tibial plateau that articulates with respect to the medial and lateral femoral condyles of the knee joint 102.

Referring to FIG. 1B, and in another example, the anatomical bone 51 having the bone defect 120 can be a glenoid 106 of a shoulder joint. In particular, the bone defect 120 can be at least partially disposed at an articular glenoid surface 104 of the glenoid 106. The glenoid surface 104 defines a glenoid cavity 108 of the shoulder joint that is configured to receive a humeral head so as to define the shoulder joint. Alternatively, the bone defect 120 can be defined by the humeral head. For instance, the bone defect 120 can be at least partially disposed at an articular surface of the humeral head.

Referring to FIG. 1C, in yet another example, the anatomical bone 51 having the bone defect 120 can be defined by an articular surface 121 of an acetabulum 110 of a hip joint. For instance, the bone defect 120 can be at least partially disposed at an articular surface of the acetabulum 110. Alternatively, the bone defect 120 can be defined by a femoral head 111 that is configured to be received by the acetabulum 110. In this regard, while the bone defect 120 has been illustrated in connection with particular articular bone surfaces of a patient's anatomy, it should be appreciated that any bone of the patient's anatomy can contain the bone defect 120. Thus the systems and methods described herein can be applied to any suitable bone of a patient as desired.

Figure 2A:
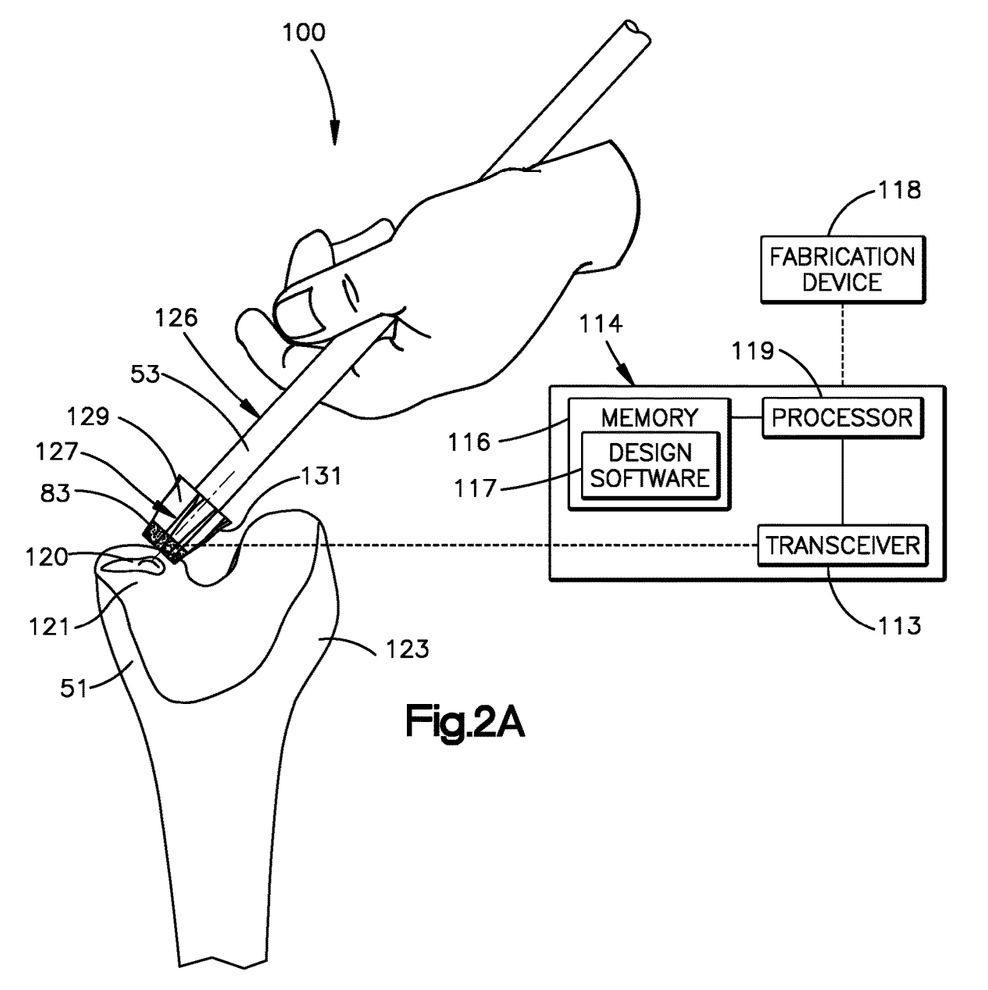
FIG. 2A is a diagrammatic illustration of an implant design system for a bone resection procedure, according to an aspect of this disclosure.
Figure 2B:
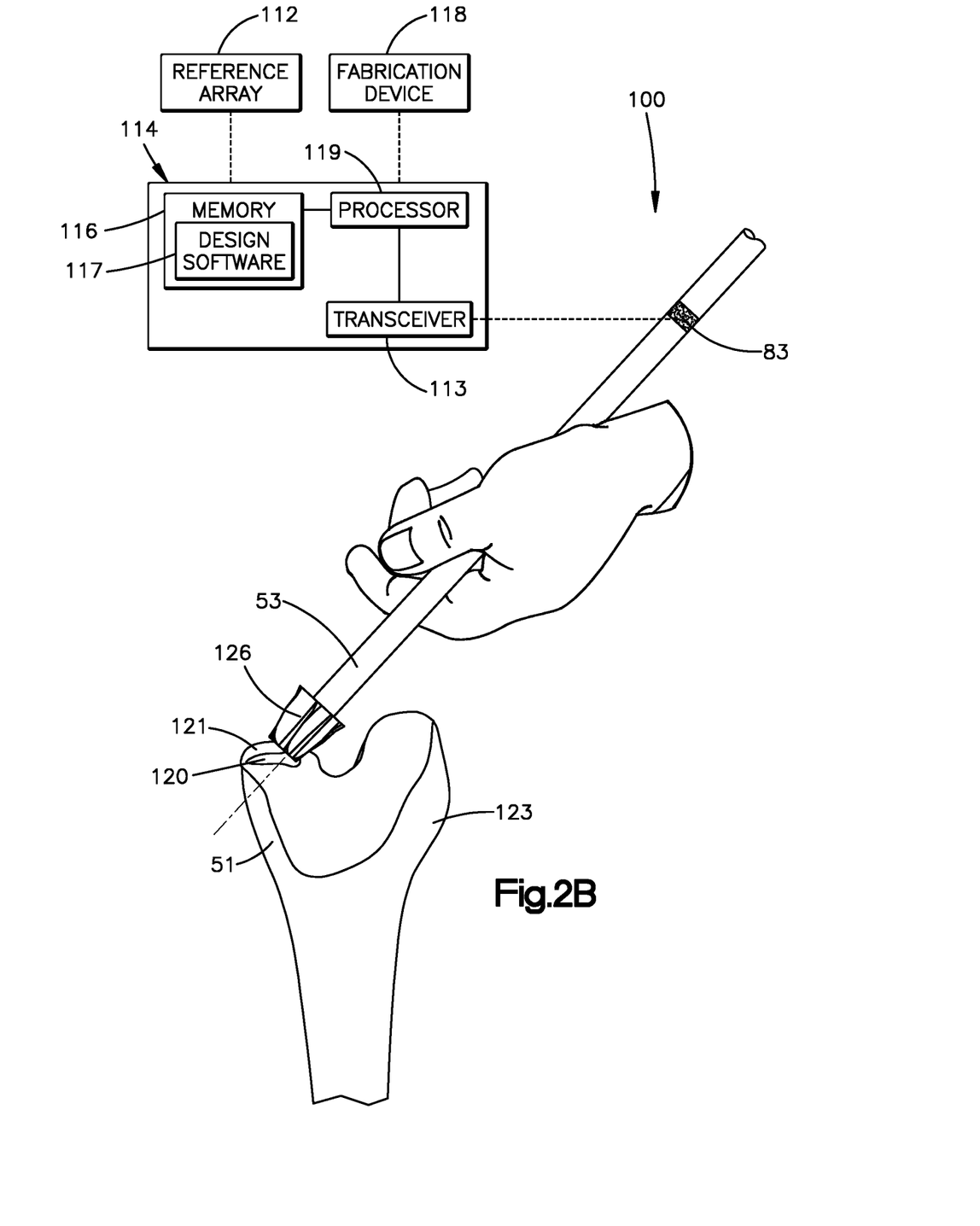
FIG. 2B is a diagrammatic illustration of an implant design system for a bone resection procedure, according to another aspect of this disclosure.

Referring now to FIGS. 2A and 2B, an implant design system 100 includes the tracker 83, a computing system 114 that is configured to determine a cutting path based on movement of the tracker 83 during operation of the cutting tool 126, and a fabrication device 118 that is configured to manufacture an implant having a size and shape that corresponds to the determined cutting path. The implant design system 100 is thus configured to design a customized implant 101 that corresponds to a cutting path of the cutting tool 126 during resection of the bone defect 120. The cutting path of the cutting tool 126 can be determined by tracking the movement of the cutting tool 126. Movement of the cutting tool 126 can be performed manually, or can be guided by any suitable guide assembly of the type described above. The implant design system 100 includes at least one tracker 83 disposed on the cutting tool 126, and a computing system 114 configured to communicate with a variety of computing or navigational systems that are known and used in the art.

The cutting tool 126 can be guided by a surgeon to remove the bone defect 120 on an articular surface 121 of the patient's bone 51. While the bone 51 is illustrated as the femoral condyle 123 in FIG. 2A, it is appreciated that the bone 51 can define an articular surface of any joint in the human body as described above. In other example, the bone can be any other bone in the human body disposed at any location of the bone where the bone defect 120 exists. The cutting tool 126 can include any suitable cutting member 129 such as a burr 131 as shown, but it is recognized that the cutting member 129 can alternatively be configured as a reamer, a saw, drill, or other suitable cutting member capable of removing bone from a patient. The cutting tool 126 can further include a tool shaft 53 that is configured to support the cutting member 129. For instance, the tool shaft 53 can orient the cutting member 129 relative to the patient's bone 51. Movement of the tool shaft 53 therefore correspondingly moves the cutting member 129 with respect to the patient's bone 51. For instance, translation of the tool shaft 53 correspondingly translates the cutting member 129. Angulation of the tool shaft 53 correspondingly changes an orientation of the cutting member 129. Thus, as shown at FIG. 2A, the tool shaft 53 can be guided by a surgeon to perform a surgical resection of the bone 51. The surgeon can guide the tool shaft 53 to the area of the bone 51 that has the defect 120 and can manually resect the defect 120.

The cutting tool 126 includes a tracker 83 that is used to track the position of the cutting tool 126 during use. The tracker 83 is configured provide data that indicates a position of the cutting member 129 and/or an orientation of the cutting member 129. In one example, the tracker 83 can be carried by the tool shaft 53, such that changes in position and/or orientation of the tool shaft 53 is tracked, and the changes in position and/or orientation of the cutting member 129 can be determined. Alternatively, as shown at FIG. 3A, the tracker 83 can be disposed directly on the cutting member 129. Thus, the tracker 83 can provide data that indicates the position and/or orientation of the cutting member 129.

Figure 3:
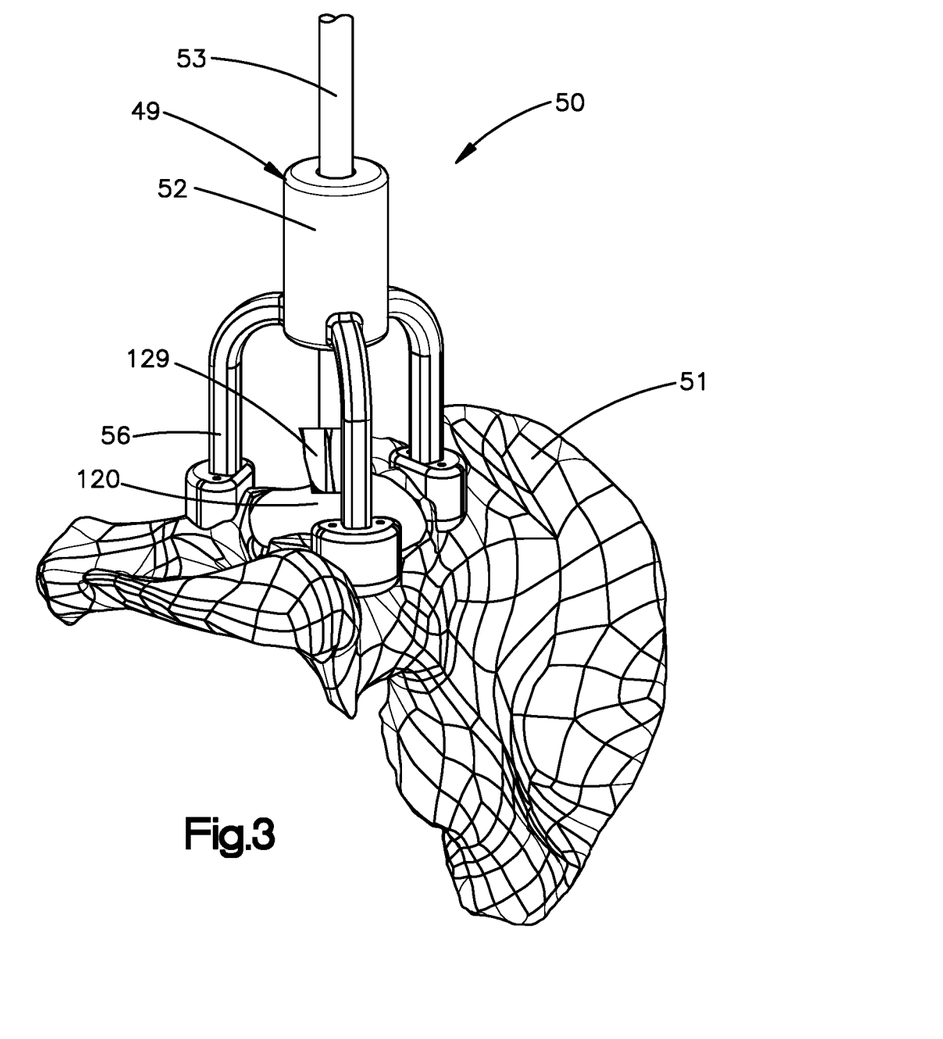
FIG. 3 is a perspective view of a tool guided by a guide assembly to a bone to be operated.

In some examples, as shown in FIG. 3, movement the cutting tool 126 can be guided by a guide assembly 50 when resecting bone. As shown, the guide assembly 50 can be configured as an acetabular guide assembly 49 that is configured to guide the cutting member 129, for instance when the bone 51 defines the acetabulum 110 shown in FIG. 1C above. During operation, the surgeon guides the cutting member 129 toward and away from the acetabulum 110. For instance, a guide member 52 can receive the tool shaft 53, and can orient the cutting member 129 relative to the patient's bone 51. The guide assembly 50 can include the guide member 52 and a plurality of arms 56 that support the guide member 52. The guide arms 56, in turn, can extend from the guide member 52 to respective locations on the patient's bone 51, such that the arms are supported by the bone 51. For instance, each of the arms 56 can be individually contoured to fitted onto respective different and separate unique locations of the bone 51. When the arms 56 are fitted onto the respective different locations of the bone 51 and the guide member 52 is supported relative to the arms 52, the guide member 52 can be similarly supported relative to the underlying bone 51.

Accordingly, the arms 56 can fixedly support the guide member 52 at a predetermined position and orientation relative to the bone 51. As a result, that the tool shaft 53 is oriented as desired when received by the guide member 52. It will be appreciated that the guide assembly 50 can include additional components, such as, for example, mounting pads, guide bodies, or still other components. While one example of the guide 50 is shown as the acetabular guide assembly 49, it is recognized that any suitable guide assembly can be provided that is configured to guide the movement of the cutting member 129 as it resects bone from any desired bone surface. The guide assembly 50 can direct linear, rotational, and/or circumferential movement of the tool shaft 53 disposed therein.

As disclosed above, the guide assembly 50 is configured to receive the tool shaft 53 in the guide member 52, such that the tool shaft 53 is movable in the guide member 52. For instance, the tool shaft 53 can be translatable and rotatable in the guide member 52. The guide member 52 thus limits translation of the tool shaft 53 to a predetermined direction, but can prevent rotation of the tool shaft 53. Alternatively, the guide member can allow rotation of the tool shaft 53, but prevent translation of the tool shaft 53. Alternatively or additionally still, the tool shaft 53 can be coupled to the guide member 52 so as to rotate about multiple axes. For instance, a ball joint can connect the tool shaft 53 to the guide member 52. Alternatively still, the guide member 52 can allow both translation and rotation of the tool shaft 53. The tool shaft 53 can be inserted directly into the guide member 52, or alternatively, the guide member 52 can retain a sleeve that can translatably and/or rotatably receives the tool shaft 53.

Referring again to FIG. 2A, the computing system 114 includes a processor 119, a sensor 113, and a memory 116 that is configured to store design software 117 among other things. The memory 116 can also store data received by the tracker 83. The memory 116 may include random access memory (RAM), read-only memory (ROM), non-volatile memory, such as electrically erasable programmable ROM (EEPROM) or flash memory, or combinations thereof. The processor 119 can comprise a general purpose processor, a special purpose processor, a conventional processor, a digital signal processor (DSP), a plurality of microprocessors, one or more microprocessors in association with a DSP core, a controller, a microcontroller, any other type of integrated circuit (IC), a state machine, and the like. The processor 119 may perform signal coding, data processing, power control, input/output processing, and/or any other functionality suitable for operation of the computing system 114 in accordance with its intended functionality. The computing system 114 may further comprise a graphics interface, a graphics processing unit (GPU), a video memory, and a video interface. These components can cooperate to display graphics and text on a video monitor 115 (see FIGS. 4A-4D) for a surgeon to view before, during, and/or after a surgical procedure.

The computing system 114, and in particular the sensor 113, is configured to locate the spatial reference points of the tracker 83 to determine the position of the cutting tool 126 relative to the bone 51. The tracker 83 can be an active tracker that sends signals to the sensor to indicate the position of the tracker 83. Alternatively, the tracker 83 can be a passive tracker, such that the sensor 113 actively senses the position of the tracker 83. The processor 119 receives signals from the sensor 113, and determines the position of the cutting member 129 based on the known location of the tracker 83 on the cutting tool 126. For instance, when the tracker 83 is disposed on the cutting member 129, then the position of the tracker 83 also defines the position of the cutting member 129. When the tracker 83 is disposed at a location having a known position relative to the cutting member 129, the processor 119 determines the position of the cutting member 129 based on the position of the tracker 83. In still other examples, for instance when the orientation of the tool shaft 53 remains constant throughout resection of the bone defect 120, the processor 119 can determine the cutting path based on changes in position of the tracker 83 without determining the position of the cutting member 129 based on the position of the tracker 83. In another example, for instance when the orientation of the tool shaft 53 changes during resection of the bone defect 120, the processor 119 can determine the orientation and position of the tracker 83 to determine the position of the cutting member 129. For example, the tracker 83 can include an optical tracker, an electromagnetic tracker, a geomagnetic tracker, or still other types of trackers that can detect orientation angles of the tracker 83. The orientation angles can include, for example, angular displacements in an x-y-z coordinate system. Based on the position of the tracker 83 on the tool shaft 53 relative to the cutting member 129 and the orientation angles of the tracker 83, the processor 119 can determine the cutting path of the cutting member 129.

In some examples, the processor 119 determines an initial position of the tracker 83 upon activation of the computing system. Subsequent positions of the tracker 83 during movement of the cutting tool 126 during operation can be determined relative to the initial position, such that the relative positions of the tracker 83 with respect to the initial position over time provides a cutting path along which the cutting tool 126 has traveled to resect the bone defect 120. Alternatively, subsequent positions of the tracker 83 are determined by comparing a current position of the tracker 83 to a previous position of the tracker 83. The positions of the tracker 83 relative to respective prior positions over time provide the cutting path along which the cutting tool 126 has traveled to resect the bone defect.

The position of the tracker 83 can be determined relative to a known reference point. The reference point can be located on the computing system 114, the guide assembly 50, or other location. The reference point can be located on the cutting tool 126 or spaced from the cutting tool 126. The position of the tracker 83 can be determined in real time, or upon an expiration of predetermined time duration. The computing system 114 can record (e.g. in the memory 116) real time information of the position and/or cutting angle of the cutting tool 126 based on communication with the tracker 83 during a surgical procedure.

With reference to FIG. 2B, the implant design system 100 can also include a reference array 112 that generates the reference point. The reference array 112 can be configured to transmit the reference point to the computing system 114. The connection between the reference array 112 and the computing system 114 can be a wired connection or a wireless connection, such that the computing system 114 can be located remotely from the reference array 112. Thus, the reference array 112 can be mounted to the guide assembly 50, mounted to the computing system 114, or positioned at another location to provide a reference point for determining the position of the tracker 83. The reference array 112 can be similar to reference arrays used by existing surgical navigation systems.

The position of the cutting tool 126 relative to the bone 51 can be determined based on the reference point. For example, a position of the reference point relative to the bone 51 can be determined. The relative position of the reference point can be calculated, measured, or other method for determining a relative position of a reference point. A distance between the tracker 83 located in the cutting tool 126 and the reference point can define spatial reference information. As the tracker 83 moves with the cutting tool 126 relative to the reference point, the spatial reference information can comprise a plurality of distances and positions of the tracker relative to the reference point. The spatial reference information and the position of the reference point relative to the bone 51 can then be used to determine the position of the cutting tool 126 relative to the bone 51. The spatial reference information, the position of the reference point, and the position of the cutting tool 126 relative to the bone 51 can be stored in the memory 116 of the computing system 114.

In an example, the tracker 83 can be configured to track a tip of the cutting tool 126 relative to the reference point during a procedure to resect bone material from the bone 51. The tip of the cutting tool 126 can be a center of the tool 126. Additionally or alternatively, the tip of the cutting tool 126 can define a cutting surface 127 of the cutting tool 126. In an aspect, the tracker 83 can be located at different locations along the tool shaft 53, or the tracker 83 can be located on or adjacent to the cutting tool 126 (see FIG. 2A). It will be appreciated that one or more trackers 83 could be included in the system 100. For example, the tool shaft 53 can include a tracker 83 and the cutting tool 126 can also include a tracker 83. The spatial reference information between the trackers 83 and the reference point can define, for example, a tool angle and/or a cutting angle of the cutting tool 126 relative to the bone 51.

The memory 116 can be configured to store the design software 117 and the instructions for fabricating a design of the customized implant 101 described herein. The design software 117 may be embodied in the form of computer executable instructions (i.e., program code, gcode, or equivalent) stored in the memory 116 which instructions, when executed by the processor 119, cause the computing system 114 to perform and/or implement the systems, methods and processes described herein. Specifically, any of the steps, operations or functions described herein may be implemented in the form of such computer executable instructions, executing on the processor 119 of the computing system 114 or other computing apparatus.

The system 100 can further include a robotic arm (not shown) that is operatively connected to the computing system 114. The tool shaft 53 can be mounted onto the robotic arm. The computing system 114 can provide control information to the robotic arm to control the tool shaft 53 during a surgical procedure to precisely adjust the tool shaft 53, as further described below. In an aspect, the robotic arm can control the tool shaft 53 without guidance from the guide assembly 50. In another example, the surgeon can perform the surgical procedure (e.g. removal of a bone defect 120) without guidance from the guide assembly 50 (see FIG. 2A).

The fabrication device 118 is configured to fabricate the customized implant 101 based on the design of the implant 101 developed by the design software 117. The fabrication device 118 can be connected to the computing system 114 to receive instructions from the computing system 114 regarding the fabrication of the implant 101. The fabrication device 118 can be in communication with the computing system 114 wirelessly or over a wire, such that the fabrication device 118 can be located remotely from the computing system 114. The fabrication device 118 can comprise an additive manufacturing device, such as a 3D printer, such that the implant 101 can be 3D printed by the fabrication device 118. The implant is fabricated according to a 3D model of the implant 101 as described in further detail below. The method of fabrication can depend on the size, shape, and overall complexity of the implant 101.

With reference to FIGS. 4A-4F and FIG. 5, a method 200 of creating a customized implant 101 for use during a surgical is described. To commence the creation of the implant 101, a model of a bone is obtained (step 202). For example, the patient's bone 51 having the bone defect 120 can be scanned. In a procedure involving the articular surface 121 with the bone defect 120, the surface can be scanned and images of the bone 51 can be stored as one or more computer files in the memory 116 of the computing system 114. The scan of the bone 51 can be performed using three-dimensional (3D) cone beam computerized tomography (CT) scanning technology, magnetic resonance imaging (MRI), ultrasound imaging, or other image data of the bone 51. The scan can include one or more 3D images of the scanned bone 51.

Figure 4A:
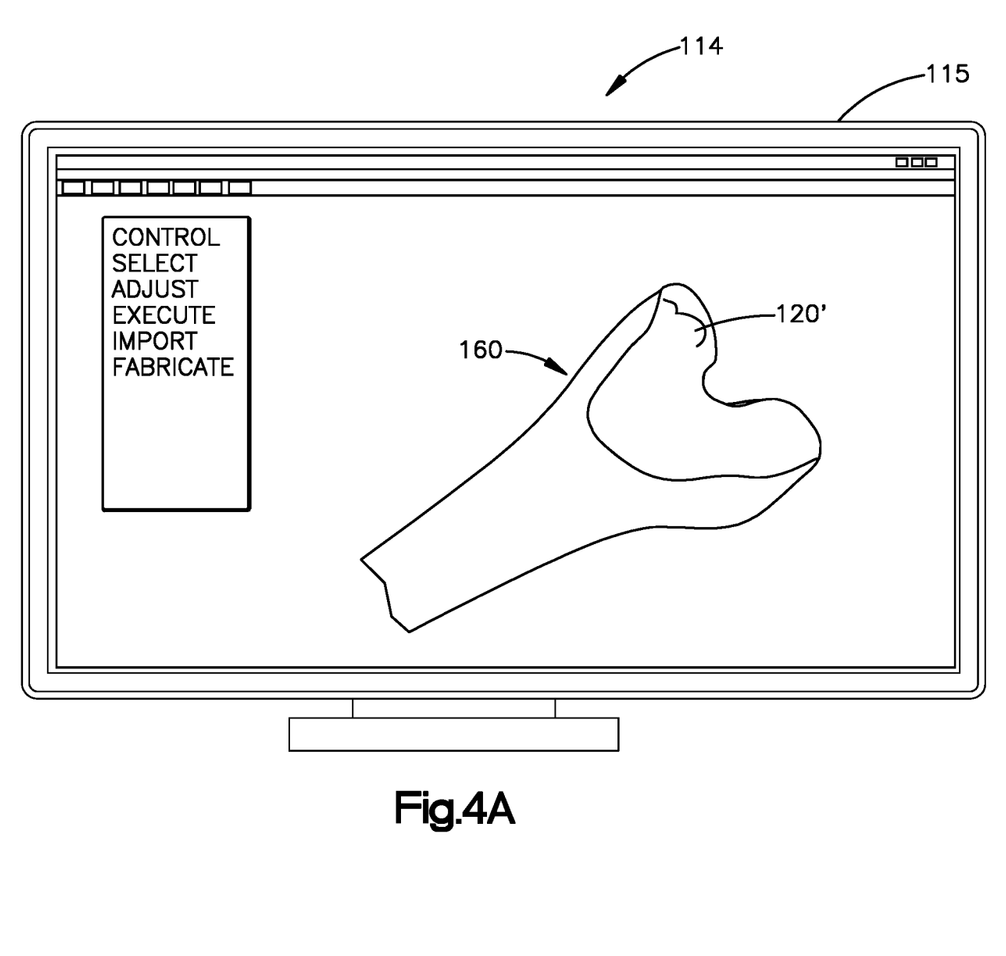
FIGS. 4A-4G illustrate an implant design system used to design an implant, according to an aspect of this disclosure.

The one or more 3D images can be used to generate a 3D model 160 of the anatomical bone 51 that includes a model of the bone defect 120' (see FIG. 4A). Using the generated 3D model 160, the bone defect 120' can be virtually resected from the bone 51, thereby creating a separate 3D model 162 of the bone 51 with bone material removed. The virtual resection may be performed prior to or during the actual surgical procedure to remove the bone defect 120 from the patient.

Based on the 3D model of the bone 51 with the virtually removed bone material, a 3D model can be generated that replaces the virtually removed bone. For example, statistical modeling algorithms can be used based on points surrounding the virtually removed bone to create an approximate geometry of a complete surface of the bone 51 (see FIG. 4B).

In an alternative aspect, instead of virtually removing the bone defect 120, the 3D model of the anatomical bone 51 can be obtained (step 202) by generating a 3D model of a generic anatomical bone (e.g. a mathematically generated 3D model). For example, the mathematically generated 3D model of the bone can be modified based on scanned points on the patient's bone, and extrapolating those points using the mathematically generated 3D model to generate a patient specific 3D model 160. Either method, or other methods, could be used to generate the 3D model 160 of the anatomical bone. The generated 3D model 160 of the bone can be referred to as the pre-existing model of the anatomical bone because it represents a model of the bone prior to the customized implant 101 being inserted. Alternative or additional techniques for generating the 3D model include, for example, principal component modelling, gaussian modelling, population-averaged geometry of the anatomical bone, or still other modelling methods.

At step 204, the bone defect 120 can be resected from the anatomical bone 51 using the cutting tool 126. The cutting tool 126 can be controlled by the surgeon and/or the robotic arm to move along a cutting path 150 during resection of the bone defect 120, thereby creating a contoured surface on the bone 51 at the location where the bone defect 120 was prior to resection. The surgeon can use the guide assembly 50 to guide the cutting tool 126 during resection. For example, referring to FIG. 3, the guide assembly 50 is shown positioned adjacent to the bone defect 120 on a surface of an acetabulum. The tool shaft 53 can be inserted into the passageway 60 of the guide assembly 50, and the surgeon can translate and rotate the cutting tool 126 as desired with the aid of the guide assembly 50. The bone defect 120 can be removed from the bone 51 by controlling the cutting tool 126 to the location on the bone 51 of the bone defect 120.

It will be appreciated that the surgeon can control the cutting tool 126 without the assistance of the guide assembly 50 (e.g. FIGS. 2A and 2B). For example, the surgeon can independently engage and guide the cutting tool 126 to the bone defect 120 without the guide assembly 50 mounted to the bone 51. The surgeon can manually move the cutting tool 126 through the bone 51 along a cutting path so as to resect the bone defect 120. The manually defined cutting path can thus define the contoured surface on the bone 51.

During resection of the bone defect 120, the cutting path 150 of the cutting tool 126 is tracked by the computing system 114 and the tracker 83 coupled to the tool shaft 53 and/or the cutting tool 126. In an aspect, the cutting path 150 can also be tracked by the reference array 112. The computing system 114 and the tracker 83 are configured to track at least a portion of the cutting path and store the at least a portion of the tracked cutting path in the memory 116 [117] of the computing system 114. In an aspect, the tracking step can include tracking a substantial entirety of the cutting path. For example, at least 75% of the cutting path can be tracked, such as at least 90%, and in one example at least 95% up to an entirety of the cutting path can be tracked. The computing system 114 can record and store the tracked cutting path in real time while the surgeon is removing the bone defect 120. The cutting path 150 can comprise point cloud data of the removed material, or other data representing a 3D space. The stored cutting path 150 can be used to generate a 3D model of the bone with the material removed (see FIG. 4C). The tracking step can further comprise tracking at least one of or both of a cutting depth of the bone 51 and an outer perimeter of the bone 51.

The tracker 83 moves along the cutting path and can actively track and store its cutting path when the surgeon or other operating personnel turn a tracking state of the tracker to "on." For example, the tracker 83 can begin tracking when the cutting tool 126 is switched "on," or when a separate tracking control is switched "on." In an alternative aspect, the tracker 83 can comprise a passive tracker, whereby an external reader is configured to track and store the position of the tracker 83. In the "on" state, the tracker 83 can begin tracking the tracked cutting path 150 and the processor 119 can store the tracked cutting path 150 in the memory 116. In an alternative aspect, the tracker 83 can begin tracking when the cutting tool 126 first engages the bone 51 and/or the bone defect 120. For example, the tool shaft 53, the cutting tool 126, or other component of the system 100 can include a sensor (not shown) configured to sense when the cutting tool 126 begins to resect bone. The sensor can include, for example, a vibration sensor, a force sensor, a rotation sensor, or other sensor configured to detect a contact between the cutting tool 126 and the bone 51 and/or bone defect 120. After the sensor senses when the cutting tool 126 begins to resect bone, a signal can be transmitted to the computing system 114 to begin recording and storing the movement of the tracker 83 in the memory 116. In an aspect, the step of tracking the cutting path can discontinue when the cutting tool 126 separates, or is otherwise spaced from, the anatomical bone 51 and/or bone defect 120.

Figure 4B:
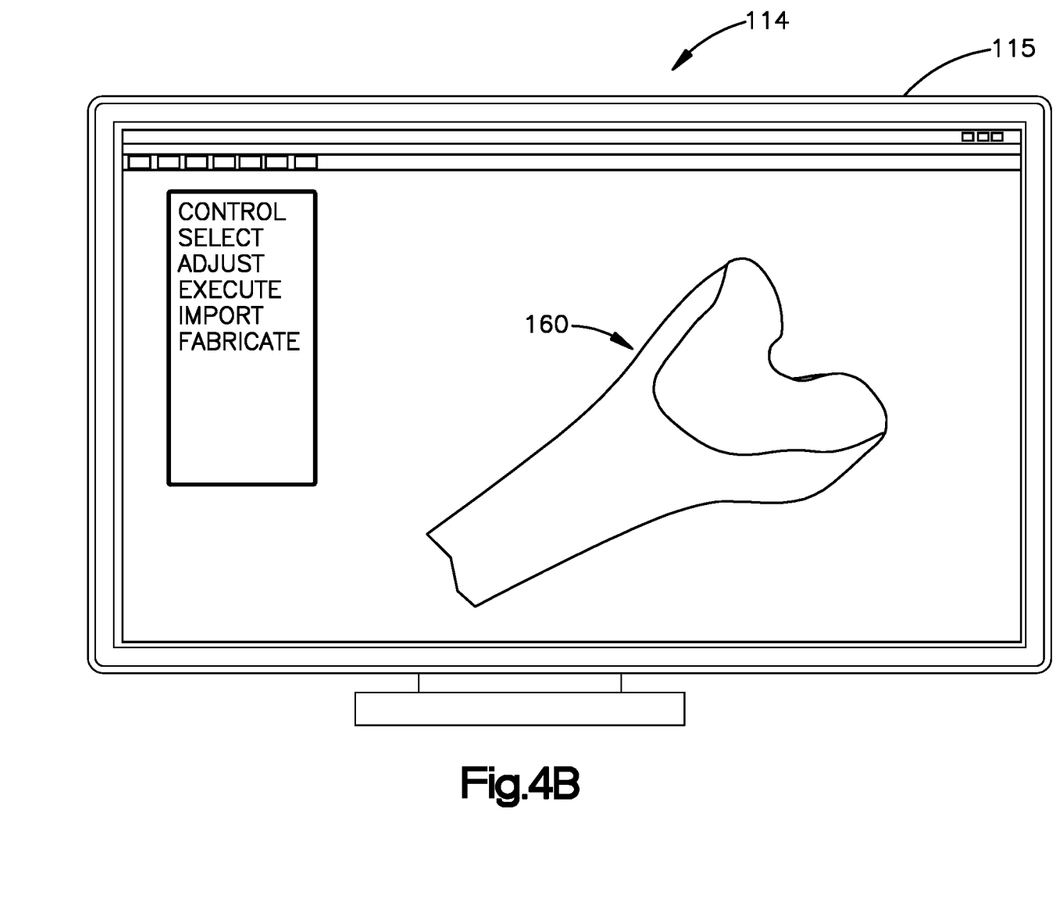
Figure 4C:
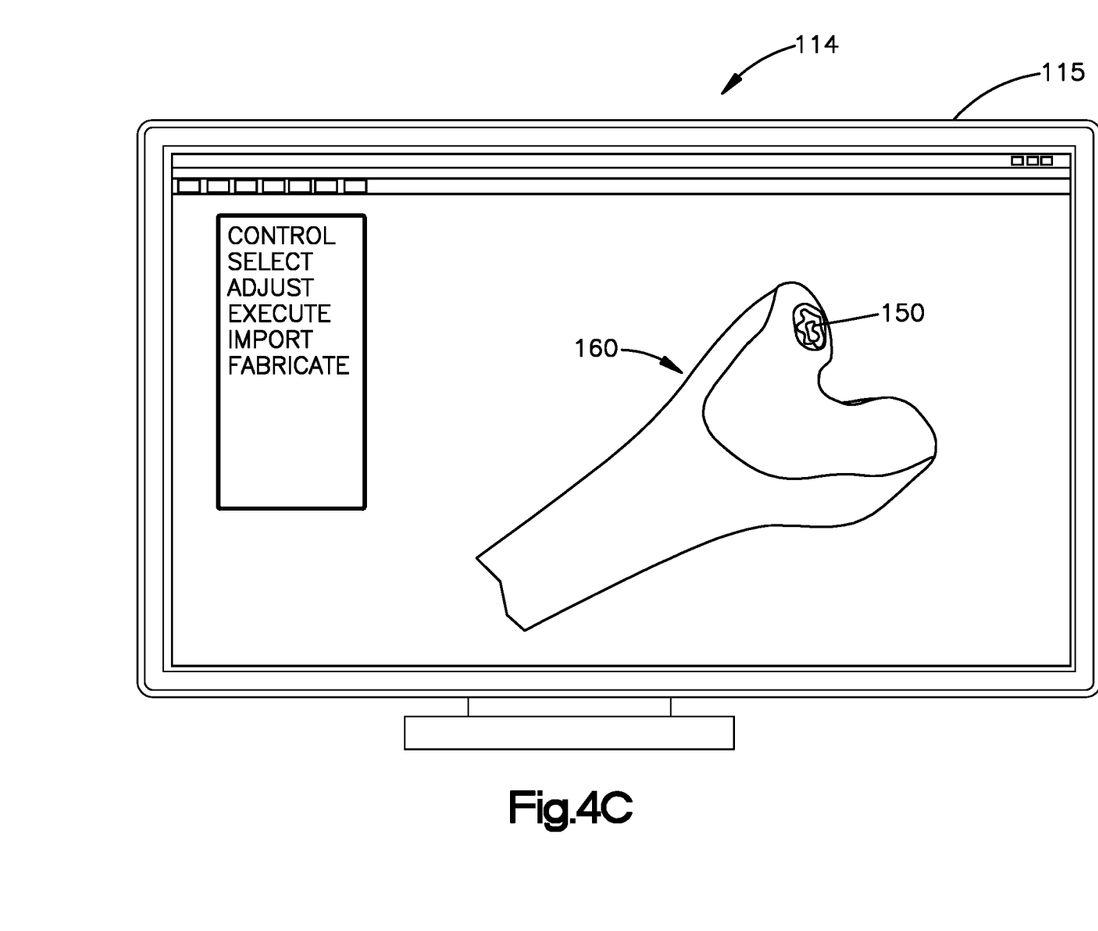
Figure 4D:
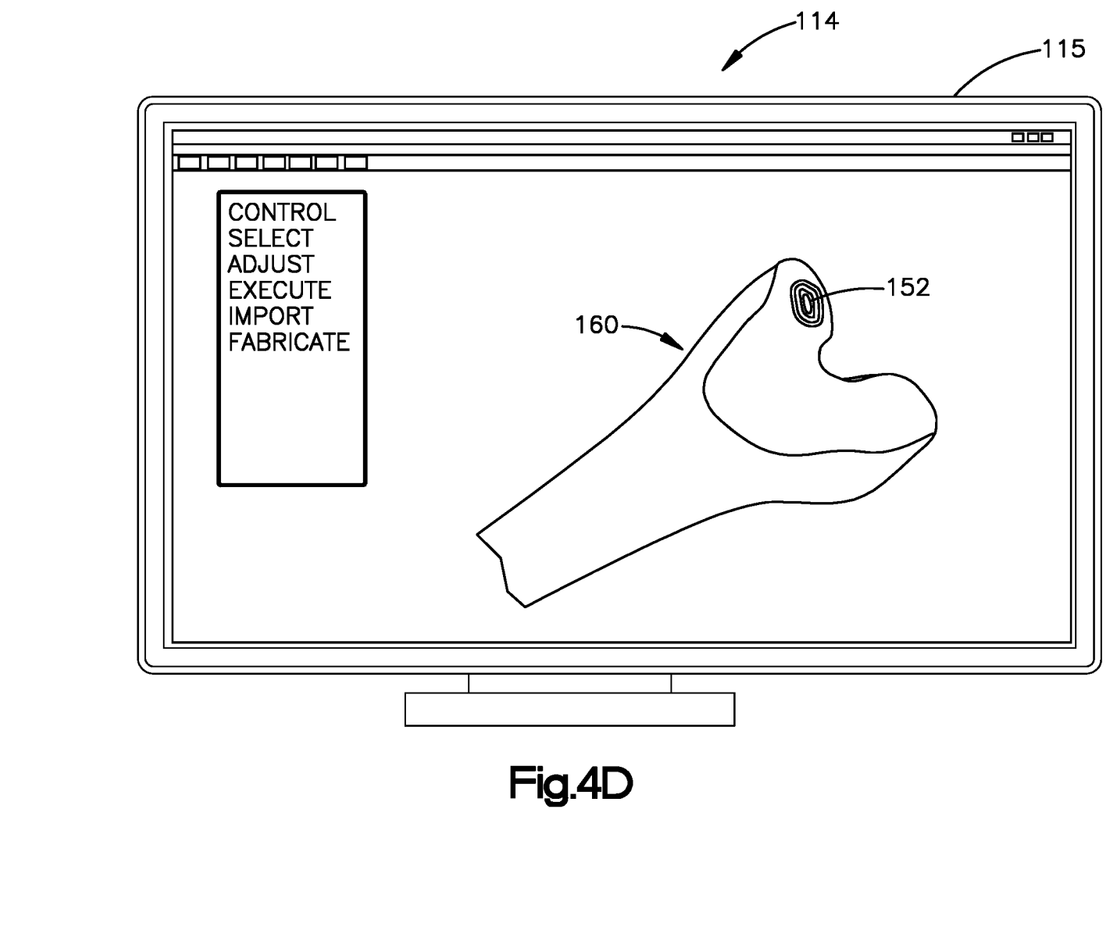
Figure 4E:
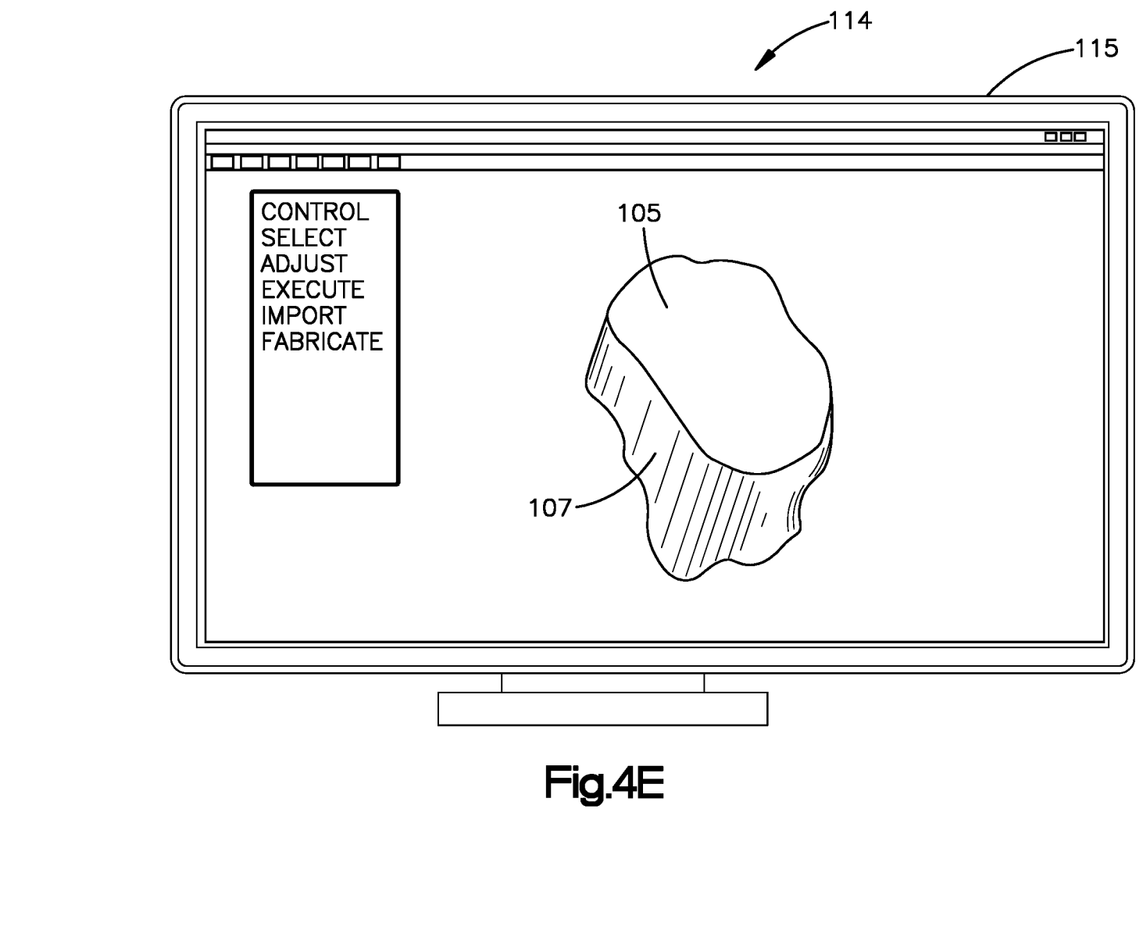

At step 206, after the cutting path 150 has been recorded and stored in memory 116, a virtual implant 105 is generated to be specific to the patient's unique anatomy. The design software 117 can generate the virtual implant 105 based at least in part on the stored cutting path 150. The physician can modify the virtual implant 105 if desired. The virtual implant 105 can include a contoured bone-facing surface 107 (see FIG. 4E) that matches the contoured bone surface 152 (see FIG. 4D) formed after removing the bone defect 120. The stored cutting path 150 can comprise data points in a 3D space of the bone removed during the surgical procedure. The 3D data points of the cutting path 150 and the virtual implant 105 can be used by the design software 117 to generate instructions for fabricating the customized implant 101. Additionally, or alternatively, the design software 117 can generate the virtual implant 105 based on the stored cutting path in combination with the pre-existing model of the anatomical bone (e.g. the model obtained at step 202). For example, the virtual implant 105 can be based on the 3D data points of the cutting path 150 and the model of a desired complete surface of the bone 51 without the bone defect 120 (FIG. 4B). Because the bone defect 120 can include protrusions and/or depressions in the bone 51, the virtual implant 105 can be modified based on the desired complete surface. For example, an outer perimeter of the virtual implant 105 can substantially correspond to the cutting path 150. Generating the virtual implant 105 can further comprise modifying the point cloud data composing the tracked cutting path to smooth the contoured bone-facing surface 107 of the virtual implant 105. Smoothing the contoured bone-facing surface 107 of the virtual implant 105 can comprise forming a continuous bone-facing surface with reduced variation in curvature.

At step 208, the customized implant 101 is fabricated based on the virtual implant 105 and the instructions for fabricating the implant 101 generated by the design software 117. In an aspect, the step of generating the virtual implant 105 can be omitted in certain examples, such that the design software 117 goes from determining an implant design based on the cutting path 150 (e.g. the determined cutting path defines the outer perimeter of the customized implant 101) without first generating the virtual implant 105. The fabrication of the implant 101 can also depend on factors including, the density of the natural bone, location of the bone, thickness and quality of the natural bone, relationship to adjacent bones, aesthetics, combinations thereof, or still other factors.

Figure 4F:
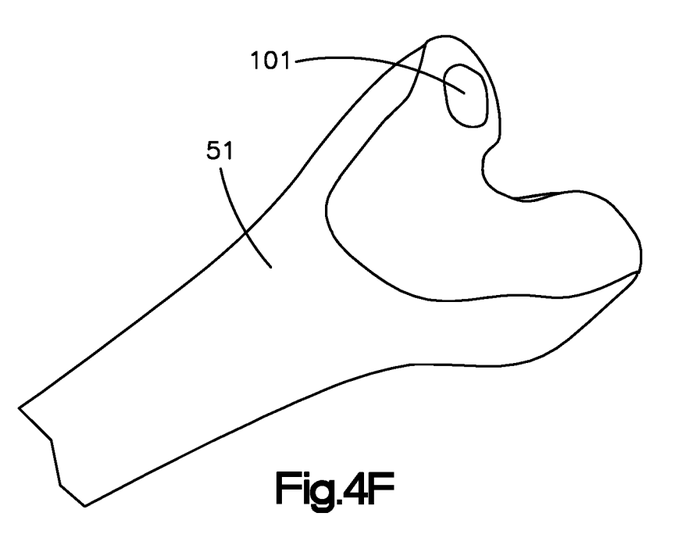

With reference to FIG. 4F, the customized implant 101 can include a bone facing surface 103 that corresponds to the contoured bone surface 152 of the anatomical bone 51. In an aspect, the bone facing surface 103 can include retentive elements (not shown), such as flexible barbs, loops, scaffolds, or other elements, positioned on or about the surface area of the implant 101. The retentive elements may be virtually designed and placed on 3D surface maps of the virtual implant 105 after considering, for example, bone density mapping, the contoured surface of the bone 51 after resection, a number, location, and size of any surface openings in the bone 51, or still other considerations. The retentive elements may be protrusive structures designed to engage the bone 51 to provide stability and anchor the implant 101 to the bone 51 during a healing stage after the implant 101 has been placed into the resected area of the bone 51. Retention can be designed to prevent movement of the implant 101 in a lateral direction, rotational direction, or about another axis. The shape and size of the retentive elements can be based on the bone density and dimension of the bone surrounding the location of resected bone. In an aspect, the minimum amount of retention necessary between the implant 101 and the bone surrounding the resected bone area should be established to reduce trauma and to speed integration.

The implant 101 may be fabricated by additive manufacturing, such as 3D printing. Alternatively, the implant 101 could be fabricated using other techniques, including, for example, computer numerical control (CNC) machining, or still other techniques. The method of fabrication can depend on the size, shape, and overall complexity of the implant 101. The implant 101 can comprise a polymer, a biocompatible additive manufacturing material, and/or other material adapted to function in close profound contact with living tissue or bone.

Figure 4G:
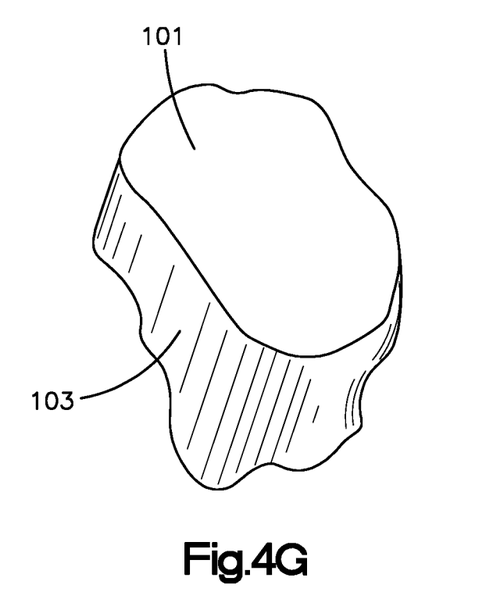
Figure 5:
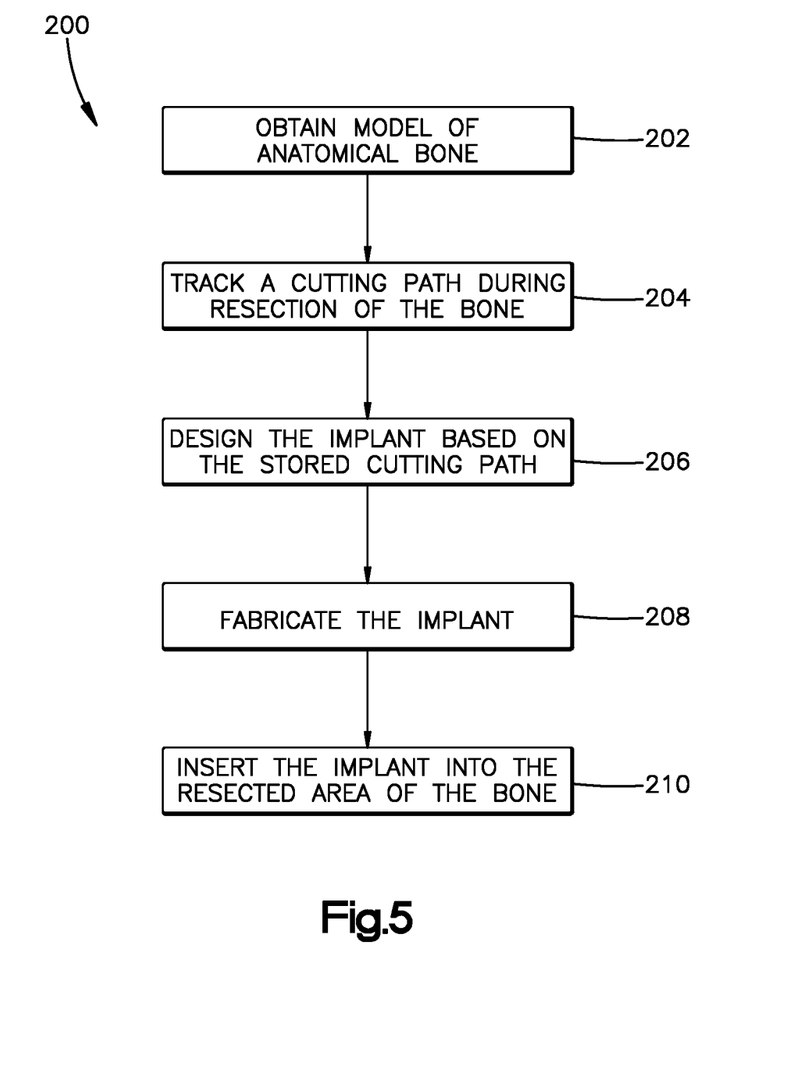
FIG. 5 illustrates a method for designing and fabricating a customized patient-specific implant, according to an aspect of this disclosure.

A physician may inspect the implant 101 prior to insertion and after the fabrication procedure. With reference to FIG. 4G, after inspection, the customized implant 101 is inserted (step 210) into the resected area of the bone 51 to replace the removed bone material and to form a new bone surface. The contoured bone-facing surface of the implant faces the contoured bone surface of the anatomical bone. An outer surface of the implant 101 can be continuous with an outer surface of the bone 51 that is adjacent the implant 101. The bone removal, implant 101 fabrication, and placement of the implant 101 within the patient may be performed in a single procedure.

In an aspect, the step of fabricating (208) the implant 101 occurs in situ. The robotic arm can fabricate the implant 101 directly onto the contoured bone surface of the anatomical bone based on the instructions generated by the design software 117. The reference array 112 can provide a reference frame by which the robotic arm can use to navigate to the location of the removed bone. A manufacturing tool can be attached to the robotic arm. The manufacturing tool can comprise a 3D printing nozzle configured to deposit the biocompatible material to form the implant 101. Based on the instructions generated by the design software 117, the computing system 114 can control the robotic arm to manufacture (e.g. print or deposit) the implant 101 directly onto the bone 51.

Although the disclosure has been described in detail, it should be understood that various changes, substitutions, and alterations can be made herein without departing from the spirit and scope of the invention as defined by the appended claims. Additionally, any of the embodiments disclosed herein can incorporate features disclosed with respect to any of the other embodiments disclosed herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A method of customizing a bone implant for an anatomical bone, the method comprising the steps of:
   operating a cutting tool along a cutting path through anatomical bone so as to resect bone from the anatomical bone, thereby defining a contoured bone surface of the anatomical bone;
   tracking at least a portion of the cutting path during the operating step, thereby defining a tracked cutting path;
   storing the at least a portion of the tracked cutting path in a memory;
   designing a virtual customized implant having a contoured bone-facing surface corresponding, at least in part, to the stored cutting path, wherein the contoured bone-facing surface substantially matches the contoured bone surface; and
   after the designing step, smoothing a bone-facing surface of the virtual customized implant, wherein the bone-facing surface of the virtual customized implant is based on the stored cutting path, to arrive at a reduced variation in curvature of the contoured bone-facing surface.

2. The method of claim 1, further comprising:
   after the designing step, generating manufacturing instructions to fabricate the implant having the contoured bone-facing surface.

3. The method of claim 2, further comprising fabricating, by a fabrication device, the implant based on the manufacturing instructions.

4. The method of claim 3, wherein the step of fabricating comprises additively fabricating the implant.

5. The method of claim 1, wherein the step of tracking is performed by a tracker, wherein the tracker begins tracking the cutting path when the cutting tool contacts the anatomical bone.

6. The method of claim 5, further comprising:
   sensing the contact between the cutting tool and the anatomical bone.

7. The method of claim 5, further comprising:
   discontinuing the step of tracking when the cutting tool separates from the anatomical bone.

8. The method of claim 1, wherein the tracking step further comprises tracking a substantial entirety of the cutting path.

9. The method of claim 1, further comprising the step of obtaining a model of the anatomical bone prior to the operating step, thereby defining a pre-existing model of the anatomical bone.

10. The method of claim 9, wherein the storing step stores the at least a portion of the cutting path in the memory as point cloud data, and the designing step further comprises applying the point cloud data to pre-existing model of the anatomical bone so as to define the contoured bone-facing surface.

11. The method of claim 9, wherein the pre-existing model is a population-averaged geometry of the anatomical bone.

12. The method of claim 10, wherein the designing step further comprises modifying the point cloud data to smooth the contoured bone-facing surface.

13. The method of claim 1, wherein the tracking step comprises tracking a tip of the cutting tool during the operating step, wherein the tip defines a cutting surface of the cutting tool.

14. The method of claim 1, wherein the cutting tool comprises a shaft and a cutting surface supported by the shaft, and the tracking step comprises tracking the shaft of the cutting tool during the operating step.

15. The method of claim 1, wherein the tracking step comprises tracking at least one or both of a cutting depth and an outer cutting perimeter created in the anatomical bone during the operating step.

16. A system configured to customize a bone implant for an anatomical bone, the system comprising:
a cutting tool configured operate along a cutting path through anatomical bone so as to resect bone from the anatomical bone, thereby defining a contoured bone surface of the anatomical bone;
a tracker configured to track at least a portion of the cutting path thereby defining a tracked cutting path, the tracker is further configured to store the tracked cutting path in a memory; and
a computing system storing an image of the anatomical bone so as to define a virtual anatomical bone having a virtual bone defect, the computing system configured to remove material from the virtual bone along the tracked cutting path so as to remove the virtual bone defect and produce a virtual contoured bone surface,
wherein the computing system comprises design software configured to design a virtual customized implant having a contoured bone-facing surface corresponding to the virtual contoured bone surface, wherein the contoured bone-facing surface substantially matches the virtual contoured bone surface, and wherein the computing system is configured to smooth the contoured bone-facing surface of the virtual customized implant that corresponds to the tracked cutting path.

17. The system of claim 16, wherein the tracker is further configured to store the tracked cutting path in the memory as point cloud data, wherein the design software is further configured to apply the point cloud data to a pre-existing model of the anatomical bone so as to define the contoured bone-facing surface.

18. The system of claim 16, further comprising:
a fabrication device configured to fabricate the bone implant based on the design of the virtual customized implant.

19. The method of claim 9, wherein the obtaining step comprises scanning the anatomical bone to define the pre-existing model of the anatomical bone.

20. The method of claim 9, further comprising the step of removing a defect from the pre-existing model to produce a model having a contoured virtual bone surface, wherein the contoured bone-facing surface is based on the stored cutting path and the model having the contoured virtual bone surface, such that the virtual customized implant matches the contoured virtual bone surface prior to the smoothing step.

* * * * *